(12) United States Patent
Collier et al.

(10) Patent No.: US 7,521,410 B2
(45) Date of Patent: Apr. 21, 2009

(54) COMPOSITIONS AND METHODS FOR IMPARTING ODOR RESISTANCE AND ARTICLES THEREOF

(75) Inventors: Robert B. Collier, Cohutta, GA (US); J. Todd Mull, Ringgold, GA (US)

(73) Assignee: ArrowStar, LLC, Dalton, GA (US)

( * ) Notice: Subject to any disclaimer, the term of this patent is extended or adjusted under 35 U.S.C. 154(b) by 266 days.

(21) Appl. No.: 10/811,202

(22) Filed: Mar. 26, 2004

(65) Prior Publication Data
US 2005/0215420 A1   Sep. 29, 2005

(51) Int. Cl.
C11D 3/37 (2006.01)
C11D 3/00 (2006.01)
C11D 3/02 (2006.01)
C11D 1/22 (2006.01)
B32B 3/02 (2006.01)
B32B 3/00 (2006.01)
B32B 9/04 (2006.01)

(52) U.S. Cl. .............. 510/276; 510/278; 510/299; 510/507; 510/357; 510/475; 510/495; 8/137; 428/85; 428/189; 428/190; 428/191; 428/543

(58) Field of Classification Search ........ 510/278, 510/475, 507, 276, 299, 357, 495; 8/137; 428/85, 189, 190, 191, 543
See application file for complete search history.

(56) References Cited

U.S. PATENT DOCUMENTS

| | | | |
|---|---|---|---|
| 3,857,727 A | 12/1974 | Benisek | 117/62 |
| 3,940,359 A | 2/1976 | Chambers | 260/29.6 |
| 4,075,178 A | 2/1978 | Turner | 528/9 |
| 4,116,885 A * | 9/1978 | Derstadt et al. | 510/299 |
| 4,161,449 A | 7/1979 | Smith et al. | 252/8.6 |
| 4,244,834 A | 1/1981 | Schwalley et al. | 252/106 |
| 4,304,675 A | 12/1981 | Corey et al. | 8/142 |
| 4,379,080 A | 4/1983 | Murphy | 510/350 |
| 4,437,429 A | 3/1984 | Goldstein et al. | 119/173 |
| 4,493,781 A | 1/1985 | Chapman et al. | 252/88 |
| 4,526,583 A | 7/1985 | Gioffre | 8/137 |
| 4,566,980 A | 1/1986 | Smith | 510/278 |
| 4,587,291 A | 5/1986 | Gardziella et al. | 524/595 |
| 4,597,800 A | 7/1986 | Turner | 106/264 |
| 4,604,110 A | 8/1986 | Frazier | 55/74 |

(Continued)

FOREIGN PATENT DOCUMENTS

JP    47-002512    1/1972

(Continued)

OTHER PUBLICATIONS

Reagan et al., "Influence of aftermarket carpet protectors on the soiling, flammability and electrical resistivity on nylon 6." Textile Chemist and Colorist 22(4):16-20 (1990).

(Continued)

Primary Examiner—Lorna M Douyon
Assistant Examiner—Jaison P Thomas
(74) Attorney, Agent, or Firm—Gardner Groff Greenwald & Villanueva, P.C.

(57) ABSTRACT

Described herein are compositions and methods for imparting odor resistance to an article. Also described herein are articles treated with the compositions and methods described herein.

62 Claims, 2 Drawing Sheets

U.S. PATENT DOCUMENTS

| | | | | |
|---|---|---|---|---|
| 4,648,882 | A | 3/1987 | Osberghaus et al. | 8/142 |
| 4,666,524 | A | 5/1987 | Smith | 106/264 |
| 4,775,588 | A | 10/1988 | Ishii et al. | 428/327 |
| 4,793,833 | A | 12/1988 | Lok et al. | 95/117 |
| 4,795,482 | A | 1/1989 | Gioffre et al. | 55/75 |
| 4,826,497 | A | 5/1989 | Marcus et al. | 604/359 |
| 4,873,000 | A | 10/1989 | Weller | 510/278 |
| 4,937,123 | A | 6/1990 | Chang et al. | 428/96 |
| 4,959,268 | A | 9/1990 | Hagiwara et al. | 428/403 |
| 5,023,140 | A | 6/1991 | Glotfelter et al. | 428/413 |
| 5,073,442 | A * | 12/1991 | Knowlton et al. | 442/94 |
| 5,120,811 | A | 6/1992 | Glotfelter et al. | 528/25 |
| 5,147,722 | A | 9/1992 | Koslow | 428/402 |
| 5,205,958 | A | 4/1993 | Swatling et al. | 252/174.13 |
| 5,211,870 | A | 5/1993 | Gilbert et al. | 252/120 |
| 5,231,063 | A | 7/1993 | Fukumoto et al. | 502/62 |
| 5,254,386 | A | 10/1993 | Simpson et al. | 428/95 |
| 5,328,766 | A | 7/1994 | Smith | 428/378 |
| 5,478,603 | A | 12/1995 | Smith | 427/393.4 |
| 5,514,302 | A * | 5/1996 | Brown | 510/280 |
| 5,516,337 | A | 5/1996 | Nguyen | 8/557 |
| 5,539,015 | A | 7/1996 | Horii et al. | 523/102 |
| 5,574,106 | A | 11/1996 | Allen | 525/183 |
| 5,622,778 | A | 4/1997 | Horii et al. | 442/118 |
| 5,629,376 | A | 5/1997 | Sargent et al. | 524/745 |
| 5,630,846 | A | 5/1997 | Hara et al. | 8/127.1 |
| 5,681,620 | A | 10/1997 | Elgarhy | 427/387 |
| 5,683,976 | A | 11/1997 | Colurciello, Jr. et al. | 510/278 |
| 5,693,385 | A | 12/1997 | Parks | 428/34.2 |
| 5,708,087 | A | 1/1998 | Buck et al. | 525/136 |
| 5,759,431 | A | 6/1998 | Nguyen | 252/8.62 |
| 5,821,177 | A | 10/1998 | Elarhy | 442/93 |
| 5,925,447 | A | 7/1999 | Gust | 428/219 |
| 5,948,480 | A | 9/1999 | Murphy | 427/393.4 |
| 5,965,264 | A | 10/1999 | Barenberg et al. | 428/402 |
| 5,980,879 | A | 11/1999 | Hiroki et al. | 424/76.1 |
| 5,981,620 | A | 11/1999 | Hammesfahr et al. | 523/116 |
| 6,028,133 | A * | 2/2000 | Peek et al. | 524/276 |
| 6,074,436 | A | 6/2000 | Wang et al. | 8/15.62 |
| 6,077,794 | A | 6/2000 | Tabata et al. | 442/123 |
| 6,096,299 | A | 8/2000 | Guarracino et al. | 424/76.1 |
| 6,159,922 | A | 12/2000 | Williams | 510/372 |
| 6,207,236 | B1 | 3/2001 | Araki et al. | 427/386 |
| 6,210,625 | B1 | 4/2001 | Matsushita et al. | 264/610 |
| 6,235,388 | B1 | 5/2001 | Yamamoto et al. | 428/364 |
| 6,242,404 | B1 * | 6/2001 | Dahanayake et al. | 510/299 |
| 6,245,833 | B1 | 6/2001 | Kang et al. | 523/203 |
| 6,262,180 | B1 | 7/2001 | Klun et al. | 525/199 |
| 6,277,408 | B1 * | 8/2001 | Wellinghoff et al. | 424/473 |
| 6,280,648 | B1 | 8/2001 | Konzelman et al. | 252/8.61 |
| 6,284,232 | B1 | 9/2001 | Calton et al. | 424/76.1 |
| 6,335,075 | B1 | 1/2002 | Seto et al. | |
| 6,369,178 | B1 | 4/2002 | McCarthy | 526/242 |
| 6,376,576 | B2 | 4/2002 | Kang et al. | 523/202 |
| 6,387,448 | B1 | 5/2002 | Collier et al. | 427/385.5 |
| 6,478,864 | B1 | 11/2002 | Field | 106/169.17 |
| 6,500,233 | B1 | 12/2002 | Miller et al. | |
| 6,521,553 | B1 | 2/2003 | Tabata et al. | 442/123 |
| 6,544,594 | B2 | 4/2003 | Linford et al. | 427/389.9 |
| 6,572,932 | B2 | 6/2003 | Sigel et al. | 427/510 |
| 6,613,862 | B2 | 9/2003 | Clark et al. | 528/49 |
| 6,833,342 | B2 * | 12/2004 | Woo et al. | 510/280 |
| 2002/0122890 | A1 | 9/2002 | Linford et al. | 427/389.9 |
| 2002/0142937 | A1 * | 10/2002 | Carter et al. | 510/507 |
| 2003/0100465 | A1 * | 5/2003 | Kilkenny et al. | 510/384 |
| 2003/0101522 | A1 | 6/2003 | Linford et al. | 8/552 |
| 2003/0104134 | A1 | 6/2003 | Linford et al. | 427/385.5 |
| 2004/0042965 | A1 | 3/2004 | Usui et al. | |
| 2004/0100125 | A1 * | 5/2004 | Ogawa et al. | 296/193.07 |

FOREIGN PATENT DOCUMENTS

| | | |
|---|---|---|
| JP | 49-099545 | 9/1974 |
| JP | 50-115284 | 9/1975 |
| JP | 8-280781 | 10/1996 |
| JP | 40-8280781 | 10/1996 |
| JP | 41-0168652 | 6/1998 |
| JP | 41-1113720 | 4/1999 |
| JP | 41-1302975 | 11/1999 |
| JP | 2-354535 | 12/2000 |
| WO | WO 84/00568 | 2/1984 |
| WO | WO 98/50619 | 11/1998 |
| WO | WO 99/57361 | 11/1999 |

OTHER PUBLICATIONS

U.S. Appl. No. 11/850,062, filed Sep. 5, 2007, Collier et al.

* cited by examiner

COMPOSITIONS AND METHODS FOR IMPARTING ODOR RESISTANCE AND ARTICLES THEREOF

FIELD OF THE INVENTION

Described herein are compositions and methods for imparting odor resistance to an article. Also described herein are articles treated with the compositions and methods described herein.

BACKGROUND OF THE INVENTION

Articles that are capable of efficiently removing chemical and other malodorous substances such as formaldehyde, acetaldehyde, ammonium and acetic acid in the air have a number of applications. For example, carpet that is capable of removing odors produced from ammonium, trimethylamine, hydrogen sulfide, methyl mercapton and acetic acid, and cigarette smoke is quite desirable.

Although the application of deodorants to articles such as carpet and textiles is known, these compositions possess various disadvantages. For example, the deodorant can be removed from the article by friction or washing and, thus, lose its deodorizing function quickly. This results in reduced efficiency of the deodorant composition. Furthermore, prior art deodorant compositions produce rigid fibers upon application to the fiber, which is also undesirable. Finally, binders present in prior art deodorant compositions may adversely react with other components or additives present in the composition, which ultimately can reduce the efficiency of the deodorant composition.

Thus, it would be desirable to produce a deodorant composition that upon application to an article is resistant to washing and wear and capable of maintaining its deodorizing function for a long time. It is also desirable that the deodorant composition be compatible with various additives and components. Finally, it is desirable that the resultant article be soft and not rigid after the article has been treated with the composition. The compositions described herein possess these advantages.

SUMMARY OF THE INVENTION

Described herein are compositions and methods for imparting odor resistance to an article. Also described herein are articles treated with the compositions and methods described herein.

Additional advantages of the compositions, methods, and articles described herein will be set forth in part in the description that follows, and in part will be apparent from the description. The advantages of the compositions, methods, and articles described herein will be realized and attained by means of the elements and combination particularly pointed out in the appended claims. It is to be understood that both the foregoing general description and the following detailed description are exemplary and explanatory only and are not restrictive of the compositions, methods, and articles described herein, as claimed.

DETAILED DESCRIPTION OF THE INVENTION

Figure 1:
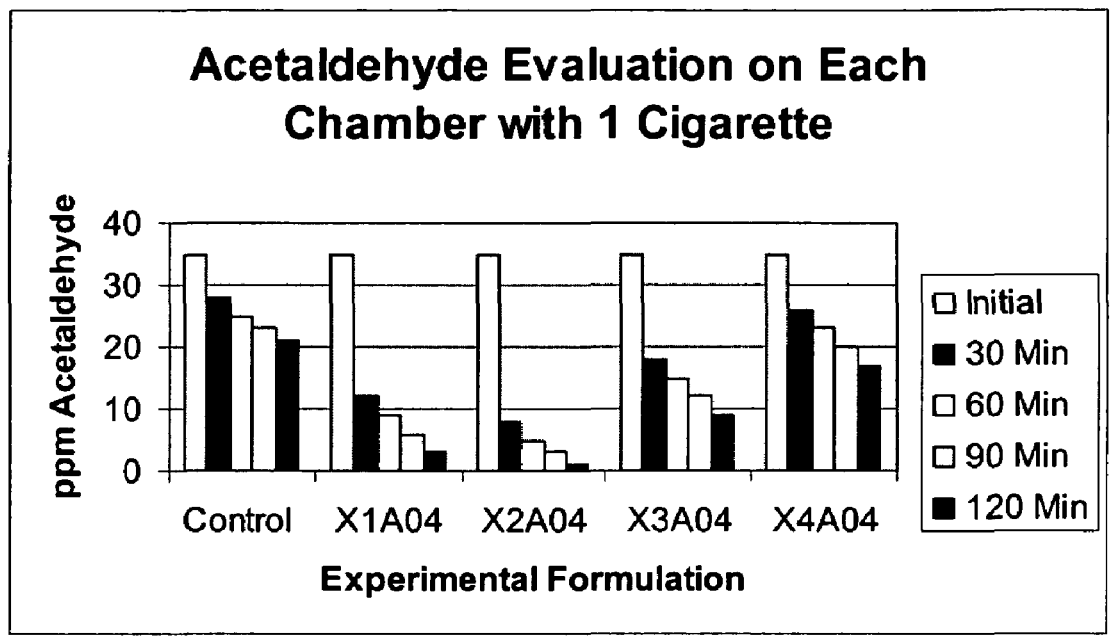
FIGS. 1-3 show measured concentrations of acetaldehyde, ammonia and pyridine, respectively, at various time intervals in the airspace located above control and treated fiber substrates during exposure to a cigarette in sealed chamber.

The compositions, methods, and articles described herein can be understood more readily by reference to the following detailed description and the Examples included herein. It is also to be understood that the terminology used herein is for the purpose of describing particular aspects only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds.

Often ranges are expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are materials and components that can be used for, can be used in conjunction with, can be used in preparation for, or are products of the disclosed compositions and methods. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a wax-modified polymer is disclosed and discussed and a number of different polyesters are discussed, each and every combination and permutation of the wax-modified polymer and the polyesters that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Throughout this application, where publications are referenced, the disclosures of these publications in their entireties are hereby incorporated by reference into this application in order to more fully describe the state of the art to which this invention pertains.

In one aspect, any of the compositions described herein can be used to impart odor resistance. In one aspect, the composition includes (a) a polyester, (b) a wax-modified polymer, and (c) a zeolite.

Any polyester known in the art can be used in the compositions described herein. The term "polyester" as used herein refers to any unit-type of polyester, including, but not limited to, homopolyesters and copolyesters (two or more types of acid and/or diol residues of monomeric units). The polyesters useful herein include an acid residue and a diol residue. The acid residue(s) of the polyester total 100 mol % and the diol residue(s) of the polyester total 100 mol %. It should be understood that use of the corresponding derivatives, specifically acid anhydrides, esters and acid chlorides of these acids is included throughout the application in the term "acid residue." In addition to the acid residue and the diol residue, the polyester can include other modifying residues. These modifying residues include, but are not limited to, a diamine, which would result in a polyester/amide. The dicarboxylic acids and diols disclosed in U.S. Pat. Nos. 6,653,440 and 6,656,601, which are incorporated by reference in their entireties, can be used herein.

In one aspect, the polyester has at least one aryl group. The term "aryl group" as used herein is any carbon-based aromatic group including, but not limited to, benzene, naphthalene, etc. The term "aryl" also includes "heteroaryl group," which is defined as an aromatic group that has at least one heteroatom incorporated within the ring of the aromatic group. Examples of heteroatoms include, but are not limited to, nitrogen, oxygen, sulfur, and phosphorus. The aryl group can be substituted or unsubstituted. The aryl group can be substituted with one or more groups including, but not limited to, alkyl, alkynyl, alkenyl, aryl, halide, nitro, amino, ester, ketone, aldehyde, hydroxy, carboxylic acid, or alkoxy. In another aspect, the polyester contains at least one terephthalic group. References proposing the use of polyesters containing terephthalate units and units derived from alkylene and polyoxyalkylene glycols for fiber or fabric treatment which are suitable for use in this invention include U.S. Pat. Nos. 3,959,230; 3,962,152; 4,027,346; 4,125,370; and 4,370,143, the disclosures of each are incorporated herein in their entireties by this reference. In one aspect, the polyester can be polyethylene terephthalate. For example, EVCOTE WR-2, which is manufactured by EvCo, can be used herein as the polyester.

In one aspect, the polyester includes a residue of dicarboxylic acids or esters, including, but not limited to, aromatic dicarboxylic acid or ester residues, aliphatic dicarboxylic acid or ester residues, or cycloaliphatic dicarboxylic acid or ester residues. In one aspect, the acid or ester residue that includes the acid moiety of the polyester includes a residue of phthalic acid; terephthalic acid; naphthalenedicarboxylic acid; isophthalic acid; cyclohexanediacetic acid; diphenyl 4,4'-dicarboxylic acid; succinic acid; glutaric acid; adipic acid; fumaric acid; azelaic acid; resorcinoldicetic acid; didiolic acid; 4,4'-oxybis(benzoic) acid; biphenyldicarboxylic acid; 1,12-dodecanedicarboxylic acid; 4,4'-sulfonyldibenzoic acid; 4,4'-methyldibenzoic acid; trans 4,4'-stilbenedicarboxylic acid; 1,2-, 1,3-, and 1,4-cyclohexanedicarboxylic acids; and mixtures thereof. In this aspect, the polyester can be prepared from one or more of the above dicarboxylic acids.

In another aspect, the dicarboxylic acid or derivative used to prepare the polyester includes, but is not limited to, terephthalic acid, 2,6-napthalenedicarboxylic acid, succinic, isophthalic, glutaric, adipic acid or ester thereof for each. In other aspects, other naphthalenedicarboxylic acids or their esters can also be used, which include, but are not limited to, the 1,2-; 1,3-; 1,4-; 1,5-; 1,6-; 1,7-; 1,8-; 2,3-; 2,4-; 2,5-; 2,6-; 2,7-; and 2,8-naphthalenedicarboxylic acids, and mixtures thereof.

In one aspect, the diol component of the polyester can include one or more residues of a diol such as, for example, a cycloaliphatic diol or an aliphatic diol. Examples of such diols include, but are not limited to, ethylene diol, diethylene diol, triethylene diol, neopentyl diol, 1,4 butanediol, 1,6 hexanediol 1,4-cyclohexanedimethanol, 1,3-propanediol, 1,10-decanediol, 2,2,4,4,-tetramethyl-1,3-cyclobutanediol, 3-methyl-2,4-pentanediol, 2-methyl-1,4-pentanediol, 2,2,4-trimethyl-1,3-pentanediol, 2-ethyl-1-1,3-hexanediol, 2,2-diethyl-1,3-propanediol, 1,3-hexanediol, 1,4-bis-(hydroxyethoxy)benzene, 2,2-bis-(4-hydroxycyclohexyl)-propane, 2,4-dihydroxy-1,1,3,3-tetramethylcyclobutaine, 2,2-bis-(3-hydroxyethoxyphenyl)propane, 2,2-bis-(4-hydroxypropoxyphenyl)propane and mixtures thereof. In another aspect, the diol component can be ethylene diol, 1,4-butanediol, neopentyl diol, cyclohexanedimethanol, diethylene diol and mixtures thereof. The diol can be modified with up to about 50 mol % and more preferably up to about 20 mol % of any of the other diols disclosed herein.

In one aspect, the polyester is substantially linear. In another aspect, the polyester can be modified with low levels of one or more branching agents. A "branching agent" is herein defined as a molecule that has at least three functional groups that can participate in a polyester forming reaction, such as hydroxyl, carboxylic acid, carboxylic ester, phosphorous-based ester (potentially trifunctional) and anhydride (difunctional). In another aspect, the polyester can be used in dry form or as a dispersion or an emulsion.

The amount of polyester present in the composition will vary depending upon the article to be treated as well as the particular polyester that is used. In one aspect, the polyester can be from 1% to 50% by weight, 1% to 40% by weight, 1% to 30% by weight, 1% to 20% by weight, 5% to 15% by weight, or 10% by weight of the composition.

In one aspect, the polyester has a glass transition temperature ($T_g$) greater than –30° C. In another aspect, the polyester has a $T_g$ greater than –25° C., greater than –20° C., greater than –15° C., greater than –10° C., greater than –5° C., or greater than 0° C. In another aspect, the $T_g$ of the polyester is from –30° C., –25° C., –20° C., –20° C., –15° C., –10° C., –5° C., or 0° C. to 5° C., 10° C., 15° C., 20° C., 25° C., 30° C., 40° C., or 50° C., where any lower $T_g$ endpoint can be combined with any upper $T_g$ endpoint. In another aspect, $T_g$ of the polyester is from 0° C. to 20° C., 0° C. to 10° C., or 15° C. to 20° C. The $T_g$ of the polyester can be calculated using techniques known in the art including, but not limited to, the ASTM-1331 method.

The compositions described herein contain a wax-modified polymer. The term "wax-modified polymer" is defined herein as a compound composed of a wax component and a polymer component, wherein the wax component and polymer component are covalently attached to one another. Not wishing to be bound by theory, the wax-modified polymer facilitates the polyester in binding the zeolite to an article. In one aspect, the wax component contains a group that can react with an amino group or a hydroxyl group. In one aspect, the wax component can be paraffin. In one aspect, any of the waxes disclosed in U.S. Pat. No. 4,566,980, which is incorporated by reference in its entirety, can be used herein as the wax component. In one aspect, the wax includes one or more of a natural wax or a synthetic wax. In one aspect, the natural wax includes animal wax (e.g., beeswax, lanolin, shellax wax, Chinese insect wax) or a mineral wax (e.g., fossil or earth waxes such as ozocerite, ceresin, or montan, or petroleum waxes such as paraffin or microcrystalline wax). In another aspect, the synthetic wax can be a polyalkylene such as an ethylenic polymer and polyol ether-esters such as Carbowax and sorbitol, a chlorinated naphthalene such as Halowax, or a hydrocarbon produced from a Fischer-Tropsch reaction.

In one aspect, the polymer component of the wax-modified polymer contains an amino group or a hydroxyl group. In one aspect, the polymer can be a melamine resin, a phenolic acid resin, a urea resin or a combination thereof. Any of the melamine resins and derivatives thereof disclosed in U.S. Pat. Nos. 5,952,447; 6,040,044, and 6,534,150 B1, which are incorporated by reference in their entireties, can be used herein. In one aspect, two or more different polymers can be used to prepare the wax-modified polymer. In one aspect, the wax-modified polymer is CEROL-EX manufactured by Clariant, which is the reaction product between paraffin and melamine resin.

The amount of wax-modified polymer present in the composition will vary depending upon the article to be treated as well as the particular wax-modified polymer that is used. In one aspect, the wax-modified polymer can be from 1% to 50% by weight, 1% to 40% by weight, 1% to 30% by weight, 1% to 20% by weight, 5% to 15% by weight, or 10% by weight. In another aspect, the wax-modified polymer can be used in dry form or in the form of an emulsion or dispersion.

The zeolite used in the compositions described herein can include any zeolite known in the art. Not wishing to be bound by theory, it is believed that the zeolite imparts the odor resistance when the composition is applied to the article. Depending upon the zeolite selected, the zeolite can mask, neutralize, absorb, or reduce odors that can be present on the article.

In general, zeolites are aluminosilicate materials. Any of the zeolites disclosed in U.S. Pat. Nos. 4,304,675; 4,437,429; 4,793,833; and 6,284,232 B1, which are incorporated by reference in their entireties, can be used herein. In one aspect, the zeolite includes a mixture of $SiO_2$, $Al_2O_3$, and $Na_2O$. In one aspect, when the zeolite includes a mixture of $SiO_2$, $Al_2O_3$, and $Na_2O$, the amount of $SiO_2$ present is from 70% to 99% by weight, 80% to 99% by weight, 90% to 99%, 90% to 95% by weight, or 92% to 95% by weight of the zeolite; the amount of $Al_2O_3$ in the zeolite is from 1% to 20% by weight, 2% to 10% by weight, 3% to 7% by weight, or from 4% to 6% by weight of the zeolite; and the amount of $Na_2O$ in the zeolite is from 0.5% to 20% by weight, 1% to 10% by weight, 1% to 8% by weight, 1% to 6% by weight, 1% to 4% by weight, or from 1% to 2% by weight of the zeolite. In one aspect, the zeolite can be mordenite. In another aspect, mordenite manufactured by Chemie Uetikon and P.Q. Corp. can be used herein.

The amount of zeolite present in the composition will vary depending upon the article to be treated as well as the particular zeolite that is used. In one aspect, the zeolite can be from 1% to 40% by weight, 1% to 30% by weight, 5% to 30% by weight, 10% to 25% by weight, or 20% by weight of the composition.

In one aspect, the polyester can be from 1% to 50% by weight of the composition, the wax-modified polymer can be from 1% to 50% by weight of the composition, and the zeolite can be from 1% to 40% by weight of the composition, wherein the sum of the amount of the polyester, the wax-modified polymer, and zeolite is less than or equal to 100%. In the case when the amount of polyester, wax-modified polymer, and zeolite is less than 100% by weight, the composition can contain one or more other components described below.

Depending upon the application of the composition, the composition can contain various other additives and components. In one aspect, the composition can optionally include a surfactant. Examples of surfactants include, but are not limited to, dispersants, emulsifiers, detergents, and wetting agents. Any of the surfactants disclosed in U.S. Pat. Nos. 4,648,882 and 5,683,976, which are incorporated by reference in their entireties, can be used herein.

In one aspect, the surfactant is anionic, cationic, or neutral. In one aspect, the anionic surfactant can be a sulfate and sulfonate, although other types, such as soaps, long-chain N-acyl sarcosinates, salts of fatty acid cyanamides or salts of ether carboxylic acids, of the type obtainable from long-chain alkyl or alkylphenyl poly-ethylene glycol ethers and chloroacetic acid, can also be used. The anionic surfactant can be used in the form of the alkali metal or alkali earth metal salt.

In one aspect, surfactants of the sulfate type can be sulfuric acid monoesters of long-chain primary alcohols of natural and synthetic origin containing from 10 to 20 carbon atoms, i.e. of fatty alcohols such as, for example, coconut oil fatty alcohols, tallow fatty alcohols, oleyl alcohol, or of $C_{10}$-$C_{20}$ oxoalcohols and those of secondary alcohols having chain lengths in the same range. Sulfated fatty acid alkanolamides and sulfated fatty acid monoglycerides are also suitable.

In another aspect, surfactants of the sulfonate type can be a salt of sulfosuccinic acid monoesters and diesters containing from 6 to 22 carbon atoms in the alcohol portions, alkylbenzene sulfonates containing $C_9$-$C_{15}$ alkyl groups and lower alkyl esters of α-sulfofatty acids, for example the α-sulfonated methyl or ethylesters of hydrogenated coconut oil fatty acids, hydrogenated palm kernel oil fatty acids or hydrogenated tallow fatty acids. Other suitable surfactants of the sulfonate type are the alkane sulfonates obtainable from $C_{12}$-$C_{18}$ alkanes by sulfochlorination or sulfoxidation and subsequent hydrolysis or neutralization or by addition of bisulfites onto $C_{12}$-$C_{18}$ olefins and also the olefin sulfonates i.e. mixtures of alkene and hydroxyalkane sulfonates and disulfonates, obtained for example from long-chain monoolefins containing a terminal or internal double bond by sulfonation with gaseous sulfur trioxide and subsequent alkaline or acidic hydrolysis of the sulfonation products.

In one aspect, the surfactant can be a disodium alpha olefin sulfonate, which contains a mixture of $C_{12}$ to $C_{16}$ sulfonates. In one aspect, CALSOFT® AOS-40 manufactured by Pilot Corp. can be used herein as the surfactant.

The amount of surfactant present in the composition will vary depending upon the article to be treated as well as the particular surfactant that is used. In one aspect, the surfactant can be from 1% to 20% by weight, 1% to 10% by weight, 1% to 8% by weight, 1% to 6% by weight, or 5% by weight of the composition.

In another aspect, any of the compositions described herein can optionally include one or more metal oxides other than zeolite. In one aspect, the metal oxide can be a transition metal oxide. In another aspect, the metal oxide is an oxide of silicon, aluminum, titanium, zirconium, zinc, or a combination thereof. The amount of metal oxide present in the composition will vary depending upon the article to be treated as well as the particular metal oxide, polyester, wax-modified polymer, and zeolite that are used. In one aspect, the metal oxide can be from 1% to 20% by weight, 1% to 10% by weight, or 5% to 10% by weight of the composition. Not wishing to be bound by theory, it is believed that the metal oxide behaves as a catalyst and regenerates the zeolite so that the zeolite can continue to impart odor resistance to the article.

In another aspect, any of the compositions described herein can optionally include (1) an anionically modified phenol formaldehyde polymer comprising a phenol moiety and a formaldehyde moiety, (2) a naphthalene condensate, (3) a lignin sulfonate, (4) a phenol sulfonate derivative, or a mixture thereof. Any of the anionically modified phenol formaldehyde polymers, naphthalene condensates, lignin sulfonates, and phenol sulfonate derivatives disclosed in U.S. Pat. No. 6,387,448 B1, which is incorporated by reference in its entirety, can be used herein.

The anionically modified phenol formaldehyde polymers appropriate for use in the compositions described herein include, but are not limited to, condensation products of aldehydes with phenyl bearing molecules and anionically modifying agents. The phenol formaldehyde polymer can be anionically modified by methods including, but not limited to, sulfonation, phosphonation and acylation. When sulfonation is desired, it can be accomplished by the use of sulfonic acid. In one aspect, the polymer contains phenylsulfonic acid residues. In other aspects, the polymer can be a condensation product of naphtholsulfonic acid and an aldehyde, an anionically modified hydroxyaromatic formaldehyde condensate, the condensation product of anionically modified dihydroxydiphenylsulfone or the condensation product of naphtholsulfonic acid or the derivatives of any of these polymers.

Examples of other suitable anionically modified phenol formaldehyde polymers or compounded materials based on phenol formaldehyde polymers include, but are not limited to, DU PONT SR-500 (Du Pont), FX 369, 668, 661 (3M), INTRATEX N (Crompton and Knowles), ERIONYL PA (Ciba-Geigy), NYLOFIXAN P and PM (formerly Sandoz, now Claraint), MESITOL NBS (formerly Mobay Chemical Corp., now Dystar, Inc.), ARROWSHIELD® GSR AND ARROWSHIELD® 2713 (Arrow Engineering), etc. In an alternative aspect, lignin sulfonates can be used in place of the anionically modified phenol formaldehdye polymer. In yet another aspect, naphthalene condensates can be used in place of the anionically modified phenol formaldehyde polymer. In yet another aspect, phenol sulphonate derivatives can be used in place of the anionically modified phenol formaldehyde polymer.

Compounds suitable for use as the anionically modified phenol formaldehyde polymer are disclosed in U.S. Pat. Nos. 4,592,940; 4,839,212; 4,822,373; 4,940,757; and 4,937,123, which are herein incorporated by this reference in their entirety and for the teachings of suitable anionically modified phenol formaldehyde polymers.

In another aspect, any of the compositions described herein can optionally include one or more binders. A "binder" as used herein is any material that facilitates the bonding of one or more components present in the composition to the article. In one aspect, the binder can be a polymeric resin. The binders disclosed in U.S. Pat. Nos. 4,775,588; 5,147,722; and 5,539,015, which are incorporated by reference in their entireties, can be used herein. In one aspect, the binder can be a polyolefin (e.g., polyethylene, polypropylene, polybutene-1, and poly-4-methylpentene-1); a polyvinyl (e.g., polyvinyl chloride, polyvinyl fluoride, and polyvinylidene chloride); a polyurethane; a polyacrylate (e.g., polyacrylate or polymethacrylate); a polyvinyl ester (e.g., polyvinyl acetate, polyvinyl proprionate, and polyvinyl pyrrolidone); a polyvinyl ether; a polyvinyl sulfate; a polyvinyl phosphate; a polyvinyl amine; a polyoxidiazole; a polytriazol; a polycarbodiimide; a copolymer or block interpolymer (e.g., ethylene-vinyl acetate copolymer); a polysulfone; a polycarbonate; a polyether (e.g., polyethylene oxide, polymethylene oxide, and polypropylene oxide); a polyarylene oxide; a polyester (e.g., a polyarylate such as polyethylene terephthalate); or a polyimide.

The amount of binder present in the composition will vary depending upon the article to be treated as well as the particular binder that is used. In one aspect, the binder can be from 0.1% to 50% by weight, 0.1% to 40% by weight, 0.1% to 30% by weight, 0.1% to 20% by weight, 0.1% to 10% by weight, or 0.1% to 5% by weight of the composition.

In another aspect, any of the compositions described herein can optionally include an aluminum polymer. The term "aluminum polymer" is defined as any polymeric material that contains at least one aluminum atom. The aluminum atom in the aluminum polymer can be covalently or ionically attached to the polymeric material. In one aspect, the polymeric material can contain at least one group that can interact with the aluminum atom either by a Lewis acid/base interaction or a Bronsted acid/base interaction. Examples of polymeric materials that can be used to produce the aluminum polymer include, but are not limited to, polyesters, polyols, polyamines, polyamides, polyurethanes, polycarbonates, polyacrylates, polymethacrylates, or a melamine-based resin. In one aspect, the polymeric material used to produce the aluminum polymer does not have any fluoro atoms or groups containing fluoro atoms covalently attached to the polymeric material. The molecular weight of the polymeric material can vary depending upon the polymer selected and its application.

The aluminum polymers can be prepared using techniques known in the art. For example, polyacrylic acid can be treated with a base to deprotonate at least one carboxylic acid group followed by the addition of an aluminum compound such as, for example, an aluminum salt, to produce aluminum polyacrylate. In one aspect, the aluminum polymer can be aluminum polyacrylate, aluminum polymethacrylate, or a combination thereof. For example, aluminum polyacrylate and aluminum polymethacrylate provided by Aldrich Chemical Company can be used herein. In one aspect, aluminum polyacrylate and aluminum polymethacrylate can be prepared from the polymerization of aluminum acrylate and aluminum methacrylate, respectively, using techniques known in the art.

The aluminum polymer can be used in various forms including, but not limited to, a solid (e.g., a powder) or a dispersion (e.g., in water or organic solvent). The amount of aluminum polymer present in the composition will vary depending upon the article to be treated as well as the particular aluminum polymer that is used.

In another aspect, any of the compositions described herein can optionally include one or more fluorocompounds. In one aspect, the fluorocompound can include, but is not limited to, fluorochemical urethanes, ureas, esters, ethers, alcohols, epoxides, allophanates, amides, amines (and salts thereof), acids (and salts thereof), carbodiimides, guanidines, oxazolidinones, isocyanurates, and biurets. Blends of these compounds are also considered useful. In another aspect, the fluorocompound can be a fluoropolymer. Examples of fluoropolymers useful herein include, but are not limited to, fluorinated acrylate and substituted acrylate homopolymers or copolymers containing fluorinated acrylate monomers interpolymerized with monomers free of non-vinylic fluorine such as methyl methacrylate, butyl acrylate, acrylate and methacrylate esters of oxyalkylene and polyoxyalkylene polyol oligomers (e.g., oxyethylene glycol dimethacrylate, polyoxyethylene glycol dimethacrylate, methoxy acrylate, and polyoxyethylene acrylate), glycidyl methacrylate, ethylene, butadiene, styrene, isoprene, chloroprene, vinyl acetate, vinyl chloride, vinylidene chloride, vinylidene fluoride, acrylonitrile, vinyl chloroacetate, vinylpyridine, vinyl alkyl ethers, vinyl alkyl ketones, acrylic acid, methacrylic acid, 2-hydroxyethylacrylate, N-methylolacrylamide, 2-(N,N,N-trimethylammonium)ethyl methacrylate, and 2-acrylamido-2-methylpropanesulfonic acid (AMPS). In another aspect, the fluoropolymer can be a urethane backbone fluoropolymer, wherein the fluoropolymer is cationic, anionic, or neutral. An example of an anionic urethane backbone fluoropolymer useful herein is ZONYL N-119 manufactured by Du Pont or ARROWTEX F10-X manufactured by Arrow Engineering.

In addition to the components discussed above, the compositions described herein can include other ingredients including, but not limited to, anionic leveling agents, cross-linking agents, optical brighteners, chelating agents, and inorganic/organic salts, foaming agents, ultra-violet absorption, enhanced lightfastness, flame retardants, odor elimination products, fillers and carriers, antisoiling or resoiling inhibitors, preservatives, thickeners, etc.

In another aspect, any of the compositions described herein optionally do not contain an amine compound or a hydrazine compound, wherein the amine compound has a particle diameter less than or equal to 20 μm. For example, any of the amine compounds and hydrazine compounds disclosed in U.S. Pat. No. 6,335,075 are not used in the compositions described herein. In another aspect, the composition is substantially in the absence of an amine compound or a hydrazine compound, wherein the amine compound has a particle diameter less than or equal to 20 μm. The phrase "substantially in the absence of" is defined herein as a composition having less than 0.5% by weight, less than 0.25% by weight, less than 0.1% by weight, less than 0.05% by weight, less than 0.025% by weight, or less than 0.001% by weight of the amine compound or hydrazine compound.

In one aspect, the composition consists essentially of the polyester, the wax-modified polymer, and the zeolite. In this aspect, it is contemplated that the composition contains small amounts of other components such, where these components do not affect one way or the other the odor-resistant properties of the composition.

In one aspect, the composition includes polyethylene terephthalate as the polyester, paraffin-melamine resin as the wax-modified polymer, and mordenite as the zeolite. In another aspect, this composition optionally contains disodium alpha olefin sulfonate as the surfactant and/or zinc oxide as the metal oxide.

In another aspect, the composition includes (a) a polyester, (b) a wax-modified polymer, and (c) activated carbon. In one aspect, the activated carbon can be derived from coconut shells.

Any of the compositions described herein can be produced by admixing the polyester, the wax-modified polymer, the zeolite or activated carbon, and one or more optional ingredients discussed above in any order. The term "admixing" is defined as the mixing of two or more components together so that there is no chemical reaction or physical interaction. The term "admixing" also includes the chemical reaction or physical interaction between any of the components described herein upon mixing to produce the composition. For example, depending upon the selection of the polyester and wax-modified polymer, it is possible that these components possess groups that can react with one another to produce a new chemical species.

The components used to produce the compositions described herein can be admixed using techniques described in the art. For example, mixers such as paddle mixers, drum mixers, auger mixers and the like can be used. In one aspect, finely divided solid constituents are initially introduced into the mixer in which they are then sprayed while mixing with the liquid constituents. In another aspect, either the solid components and/or the liquid components are premixed prior to their introduction into the mixer. In one aspect, after thorough blending of the finely divided solid constituents with the liquid constituents, a smooth flowable powder or liquid is produced.

In one aspect, any of the compositions described herein can be applied to an article using techniques known in the art to impart odor resistance. The method for contacting the article with the composition will vary depending upon the article and the form of the composition.

In one aspect, any of the compositions described herein can be applied to an article using techniques known in the art. The method for contacting the article with the composition will vary depending upon the article and the form of the composition. In one aspect, the compositions described herein can be in the form of an aqueous medium or a dispersion, such as a foam. Alternatively, the compositions described herein can be dissolved or dispersed in an organic solvent such as, for example, a glycol or polyether, or an aqueous organic solvent. In this aspect, the composition can be applied to the article by spray application. In another aspect, other methods such as, for example, Beck application, Continuous Liquid and Foam application, Flood, Flex Nip and Pad applications can be used to contact the article with the composition.

In another aspect, when the contacting step involves topical coating, the coating step can be performed by spray, foam, kiss or liquid injection methods and various methods thereof followed by drying in a hot air or radiant heat oven at 160 to 320° F. for a time sufficient to dry the article. In one aspect, a spray application can be applied in a liquid medium (water and chemical treatment) with a wet pickup of 5% to about 200% followed by drying. In another aspect, a foam application can be applied in a liquid medium (water and chemical treatment) with a wet pickup of 5% to about 200%. In this aspect, the foam can be applied by a direct puddle application with a press roll, an injection manifold and/or a sub-surface extraction device. Subsequent drying in a hot air or radiant heat oven at 160 to 320° F. for a time sufficient to dry the article should follow.

The prevailing plant conditions will also affect the amount of composition to be applied to the article to achieve the desired odor resistance. The composition of the article will also influence the amount of composition to be applied.

Application conditions such as pH, temperature, steam and drying time can vary. In one aspect, the pH range for the compositions described herein is from about 1.0 to about 11.0. Still further, the pH of the compositions of the present invention can be from 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5 or 11.0 where any value can be used as an upper or a lower endpoint, as appropriate. As would be recognized by one of ordinary skill in the art, the amount of pH adjustment needed prior to use of the compositions will depend on the amount of each component in the composition. Further, pH adjustment of the composition prior to use can be by methods known to one of ordinary skill in the art, such as the addition of acid or base, as appropriate.

The temperature at which the article is contacted by the compositions described herein range from ambient to temperatures up to 100° C. at atmospheric pressure and above 100° C. under pressure conditions (closed atmosphere). Still further, the temperature of application can be from 25, 35, 45, 55, 65, 75, 85 or 100° C., where any value can form an upper or a lower end point, as appropriate.

Where production procedures warrant, steam can aid in the efficacy of the compositions herein when applied by, but not limited to Beck, Continuous liquid, Flood, Flex Nip and Pad applications. The steam time can vary from about 15 seconds to about 10 minutes, or from about 2 minutes to about 8 minutes. Still further, the application time can be from about 15 seconds or 1, 2, 3, 4, 5, 6, 7, 8, 9 or 10 minutes, where any value can form an upper or a lower end point, as appropriate. In certain applications, but not limited to Spray Application and Foam Application, drying with forced heat can aid in the fixing of the composition to the article. In one aspect, the coated article can be dried with forced air. In another aspect, the coated article can be dried with microwave heat. The drying time is generally dependent upon varying conditions predicated by moisture content, range speed, type construction, the weight of the substrate, etc. The drying time can vary from 30 seconds to 15 minutes. Still further, the drying time can be from 15 seconds or 1, 3, 5, 7, 9, 10, 12, or 15 minutes, where any value can be used as an upper or lower endpoint, as appropriate.

In one aspect, the weight ratio of the composition can vary between 0.5% to 600% of wet pick up where such amount is based on the weight of the article and the composition that is used. The weight ratio will vary dependent on the manner of application. In other aspects, the owf ("on weight fiber") amount of the composition that can be applied to the article is from 0.05, 0.1, 0.2, 0.5, 1, 2, 3, 4, 5, 6, 7, 8, 9, 10, 30, 50, 70, 100, 120, 150, 200, 250, 300, 350, 400, 450, 500, 550 or 600% as measured by weight of the article, where any value can be used as an upper or lower endpoint, as appropriate. In one aspect, the owf amount of the composition that is applied to the article is from 0.5% to 5.0%.

In one aspect, once the article has been contacted with the composition, the article can be further treated to remove any composition that is not bound to the article.

Also contemplated are articles treated with any of the compositions described herein. In one aspect, the article can be composed of any material that can receive and that will adhere to the composition where odor-resistance is desirable. Examples of articles include, but are not limited to, bedding (e.g., blankets, sheets, pillowcases, futon or comforter covers, comforter wadding), clothes (e.g., suits, uniforms, shirts, blouses, trousers, skirts, sweaters, socks, panty hoses, shoe linings, shoe sole inserts), curtains, carpet, diapers, incontinent pads, surgical sponges and dressings, surgical pads, or catamenial devices such as sanitary napkins, shields, liners, or tampons.

In one aspect, the article is composed of natural and/or synthetic fibers. In one aspect, the synthetic fiber includes, but is not limited to, polyamide fibers, synthetic fibers containing free amino groups, and derivatives thereof such as nylon covered with polypropylene. Fibers containing free amino groups can be obtained by a variety of methods, including, but not limited to, the condensation reaction of hexamethylenediamine with adipic acid, hexamethylenediamine with sebacic acid, x-aminodecanoic acid, caprolactam and dodecylcaprolactam. Fibers formed from polyaryl amides, including type 6 and type 6,6 nylons, can be treated by the compositions and methods described herein. Examples of natural fibers include, but are not limited to, cotton, wool, and flax. Semi-synthetic fibers such as rayon can also be contacted with any of the compositions described herein.

The fibers treated with the compositions and methods described herein can be twisted, woven, tufted and sewn into various forms of textile materials including, but not limited to, rugs, carpets, and yarns. The fibers can be treated and then formed into the various forms of textile materials, or the formed textile can be treated.

In one aspect, the article can contain one or more fluorocompounds prior to treatment with any of the compositions described herein. In this aspect, these articles are referred to herein as fluorinated articles, wherein the article has at least one fluoro group. In one aspect, when the article is a fiber, the fluorocompound can be extruded with the material used to make the fiber so that the resultant fiber contains the fluorocompound incorporated throughout the fiber. Any of the fluorocompounds described above can be used in this aspect. The number or amount of fluoro groups present in the fluorinated article will vary depending upon the article and the fluorocompound selected. In one aspect, the amount of fluoro groups present in the fluorinated article can be from 20 ppm to 5,000 ppm, 50 ppm to 5,000 ppm, 100 ppm to 5,000 ppm, 150 ppm to 5,000 ppm, 200 ppm to 5,000 ppm, 200 ppm to 4,000 ppm, 200 ppm to 3,000 ppm, 200 ppm to 2,000 ppm, or 200 ppm to 1,000 ppm.

In one aspect, the compositions described herein can impart odor resistance to an article. The term "odor resistance" is defined herein as the ability of the compositions described herein to neutralize, absorb, or reduce odors that can be present on or near the article. The term "odor resistance" is also defined herein as the ability of the compositions described herein to chemically convert malodorous molecules to molecules that have no odor or reduced odor. For example, the compositions described herein can chemically degrade an organic molecule to smaller, non-odorous molecules.

EXAMPLES

The following examples are put forth so as to provide those of ordinary skill in the art with a complete disclosure and description of how the compositions of matter and methods claimed herein are made and evaluated, and are not intended to limit the scope. Efforts have been made to insure accuracy with respect to numbers (e.g., amounts, temperature, etc.) but some errors and deviations should be accounted for. Unless indicated otherwise, parts are by weight, temperature is in ° C. or is at room temperature and pressure is at or near atmospheric.

The scope of the present experiment is to provide odor elimination properties to polyamide fibers. The substrates utilized for the trials are nylon type 6 solution dyed fiber provided by BASF as Zeftron Z2000.

Experimental formulations utilized for the trial are the following:

| Components | X1A04 | X2A04 | X3A04 | X4A04 |
|---|---|---|---|---|
| Water | 53.4% | 37.9% | 68.7% | 80.9% |
| Evcote WR-2 (Supplied by Evco Research) | 18.3% | 25.2% | 13.4% | 10.8% |
| Calsoft AOS-40 (Supplied by Pilot Chemical) | 3.4% | 4.1% | 2.7% | 1.3% |
| Amphoterge K-2 (Supplied by Rhone Poulenc) | 2.1% | 2.8% | 1.3% | 0.5% |
| Cerol EX (Supplied by Clariant Corp) | 12.6% | 14.7% | 8.6% | 5.3% |
| Mordenite Zeolite (Supplied by Uetikon Chemie) | 10.2% | 15.3% | 5.3% | 1.2% |

Figure 2:
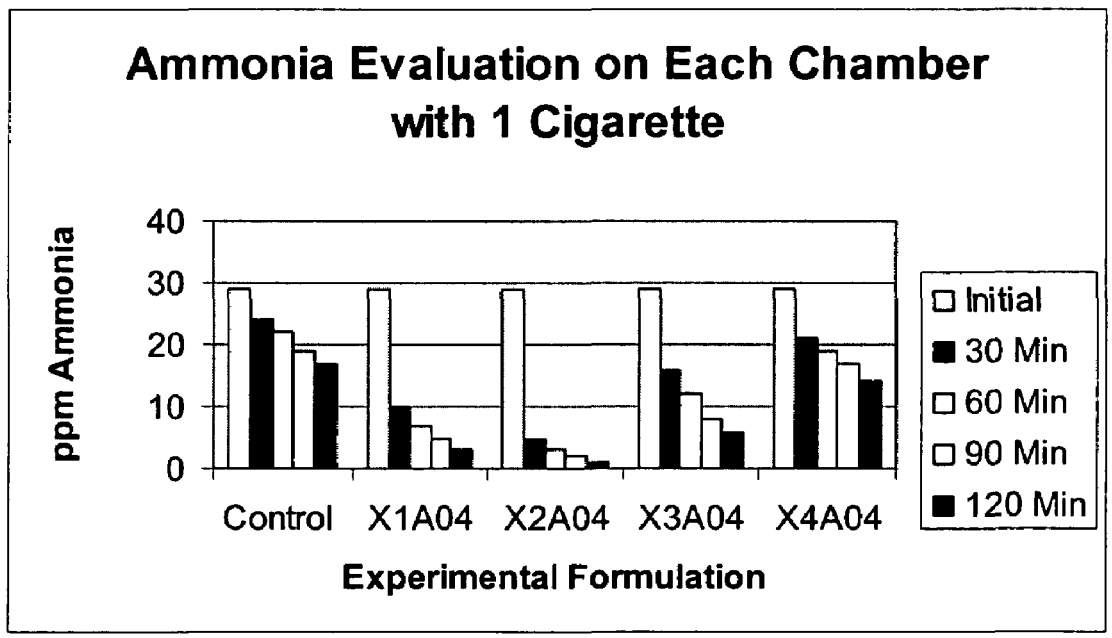
Figure 3:
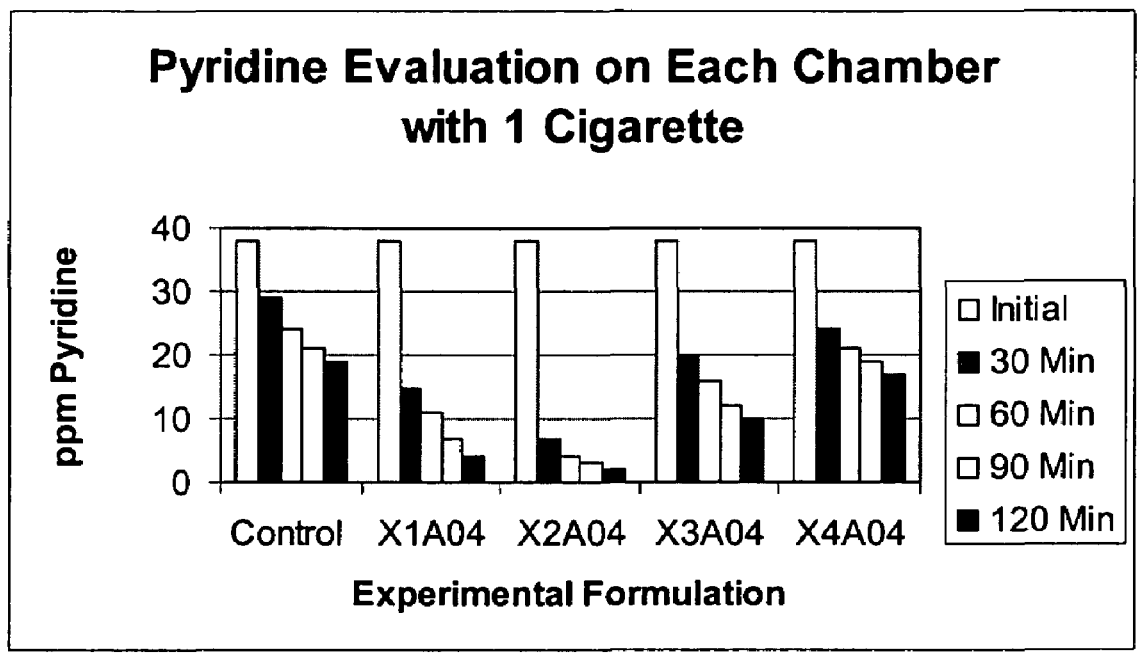

Trial marked as control in Tables 1-3 and FIGS. 1-3 had no treatment.

The above formulations were applied by topical coating spray application at a 20% wet pick up. All solutions were diluted to deliver 20 grams of each formulation per square yard of tufted fiber. The solution was applied to the fiber by topical spray and entered into a curing oven for 5 minutes at 250° F.

Next, each treated article was placed into a sealed chamber. A commercially available Marlboro Light cigarette was placed into each chamber and ignited. With the chamber sealed, an immediate air sample was taken to analyze the amount of acetaldehyde, ammonia, and pyridine present in the airspace above the tufted fiber substrate. Every 30 minutes, a sample of air from each chamber was taken to analyze the amount of acetaldehyde, ammonia, and pyridine present. Each sample of air was analyzed every 30 minutes for 2 hours giving a total of 5 readings, including the initial reading. Table 1 and FIG. 1 show the results for acetaldehyde, Table 2 and FIG. 2 show the results for ammonia, and Table 3 and FIG. 3 show the results for pyridine.

TABLE 1

|         | Control | X1A04 | X2A04 | X3A04 | X4A04 |
|---------|---------|-------|-------|-------|-------|
| Initial | 35      | 35    | 35    | 35    | 35    |
| 30 Min  | 28      | 12    | 8     | 18    | 26    |
| 60 Min  | 25      | 9     | 5     | 15    | 23    |
| 90 Min  | 23      | 6     | 3     | 12    | 20    |
| 120 Min | 21      | 3     | 1     | 9     | 17    |

TABLE 2

|         | Control | X1A04 | X2A04 | X3A04 | X4A04 |
|---------|---------|-------|-------|-------|-------|
| Initial | 29      | 29    | 29    | 29    | 29    |
| 30 Min  | 24      | 10    | 5     | 16    | 21    |
| 60 Min  | 22      | 7     | 3     | 12    | 19    |
| 90 Min  | 19      | 5     | 2     | 8     | 17    |
| 120 Min | 17      | 3     | 1     | 6     | 14    |

TABLE 3

|         | Control | X1A04 | X2A04 | X3A04 | X4A04 |
|---------|---------|-------|-------|-------|-------|
| Initial | 38      | 38    | 38    | 38    | 38    |
| 30 Min  | 29      | 15    | 7     | 20    | 24    |
| 60 Min  | 24      | 11    | 4     | 16    | 21    |
| 90 Min  | 21      | 7     | 3     | 12    | 19    |
| 120 Min | 19      | 4     | 2     | 10    | 17    |

It will be apparent to those skilled in the art that various modifications and variations can be made without departing from the scope or spirit of the compositions, methods, and articles described herein. Other aspects will be apparent to those skilled in the art from consideration of the specification and practice of the aspects disclosed herein. It is intended that the specification and examples be considered as exemplary only.

What is claimed is:

1. A composition comprising (a) a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy; (b) a wax-modified polymer, wherein the wax-modified polymer comprises a wax and a polymer, wherein the wax is covalently bonded to the polymer; and (c) a zeolite, wherein the polyester has a glass transition temperature greater than −30° C.

2. The composition of claim 1, wherein the polyester comprises polyethylene terephthalate.

3. The composition of claim 1, wherein the glass transition temperature is greater than −20° C.

4. The composition of claim 1, wherein the glass transition temperature is from −30° C. to 50° C.

5. The composition of claim 1, wherein the polyester comprises from 1% to 50% by weight of the composition.

6. The composition of claim 1, wherein the wax comprises paraffin.

7. The composition of claim 1, wherein the polymer comprises one or more of a phenolic resin or a urea resin.

8. The composition of claim 1, wherein the polymer comprises a melamine resin or a derivative thereof.

9. The composition of claim 1, wherein the wax-modified polymer comprises a paraffin-melamine resin.

10. The composition of claim 1, wherein the wax-modified polymer comprises from 1% to 50% by weight of the composition.

11. The composition of claim 1, wherein the zeolite comprises a mixture of $SiO_2$, $Al_2O_3$, and $Na_2O$.

12. The composition of claim 1, wherein the zeolite comprises mordenite.

13. The composition of claim 1, wherein the zeolite comprises from 1% to 40% by weight of the composition.

14. The composition of claim 1, wherein the polyester comprises from 1% to 50% by weight of the composition, the wax-modified polymer comprises from 1% to 50% by weight of the composition, and the zeolite comprises from 1% to 40% by weight of the composition, wherein the sum of the amount of the polyester, the wax-modified polymer, and zeolite is less than or equal to 100%.

15. The composition of claim 1, wherein the composition further comprises a surfactant.

16. The composition of claim 15, wherein the surfactant comprises a neutral surfactant or cationic surfactant.

17. The composition of claim 15, wherein the surfactant comprises an anionic surfactant.

18. The composition of claim 15, wherein the surfactant comprises a sulfonated surfactant.

19. The composition of claim 15, wherein the surfactant comprises a disodium alpha olefin sulfonate.

20. The composition of claim 15, wherein the surfactant comprises from 1% to 2% by weight of the composition.

21. The composition of claim 1, wherein the composition further comprises one or more of a metal oxide or the salt thereof, wherein the metal oxide is not a zeolite.

22. The composition of claim 21, wherein the metal oxide comprises an oxide of silicon, aluminum, titanium, zirconium, or a combination thereof.

23. The composition of claim 21, wherein the metal oxide comprises zinc oxide.

24. The composition of claim 21, wherein the metal oxide comprises from 1% to 20% by weight of the composition.

25. The composition of claim 1, wherein the composition further comprises a solvent.

26. The composition of claim 25, wherein the solvent comprises an organic solvent, water, or a combination thereof.

27. The composition of claim 1, wherein the composition further comprises an anionically modified phenol formaldehyde polymer comprising a phenol moiety and a formaldehyde moiety, a naphthalene condensate, a lignin sulfonate, a phenol sulfonate derivative, a fluorocompound, a metal oxide, an aluminum polymer, a binder, or a combination thereof.

28. The composition of claim 1, wherein the composition is substantially in the absence of a hydrazine compound or an amine compound, wherein the amine compound has a particle diameter less than or equal to 20 μm.

29. The composition of claim 1, wherein the composition does not contain a hydrazine compound or an amine compound, wherein the amine compound has a particle diameter less than or equal to 20 µm.

30. The composition of claim 1, wherein the composition consists essentially of the polyester, the wax-modified polymer, and zeolite.

31. The composition of claim 1, wherein the polyester comprises polyethylene terephthalate, the wax-modified polymer comprises a paraffin-melamine resin, and the zeolite comprises mordenite.

32. The composition of claim 31, wherein the composition further comprises disodium alpha olefin sulfonate.

33. The composition of claim 32, wherein the composition further comprises zinc oxide.

34. The composition of claim 1, wherein each aryl group is unsubstituted.

35. A method for imparting odor-resistance to an article, comprising contacting the article with the composition of claim 1.

36. An article comprising the composition of claim 1.

37. The article of claim 36, wherein the article comprises carpet.

38. A composition comprising (a) a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy; (b) a wax-modified polymer, wherein the wax-modified polymer comprises a wax and a polymer, wherein the wax is covalently bonded to the polymer; and (c) a zeolite, wherein the composition is substantially in the absence of an amine compound or a hydrazine compound, wherein the amine compound has a particle diameter less than or equal to 20 µm.

39. A method for imparting odor-resistance to an article, comprising contacting the article with the composition of claim 38.

40. An article comprising the composition of claim 38.

41. A composition comprising (a) a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy; (b) a wax-modified polymer, wherein the wax-modified polymer comprises a wax and a polymer, wherein the wax is covalently bonded to the polymer; and (c) a zeolite, wherein the composition does not contain an amine compound or a hydrazine compound, wherein the amine compound has a particle diameter less than or equal to 20 µm.

42. A method for imparting odor-resistance to an article, comprising contacting the article with the composition of claim 41.

43. An article comprising the composition of claim 41.

44. A composition comprising (a) a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy; (b) a wax-modified polymer, wherein the wax-modified polymer comprises a wax and a polymer, wherein the wax is covalently bonded to the polymer; and (c) a zeolite, wherein the zeolite comprises a mixture of $SiO_2$, $Al_2O_3$, and $Na_2O$.

45. A method for imparting odor-resistance to an article, comprising contacting the article with the composition of claim 44.

46. An article comprising the composition of claim 44.

47. A composition comprising (a) a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy; (b) a wax-modified polymer, wherein the wax-modified polymer comprises a wax and a polymer, wherein the wax is covalently bonded to the polymer; and (c) activated carbon, wherein the polyester has a glass transition temperature of greater than −30° C.

48. A method for imparting odor-resistance to an article, comprising contacting the article with the composition of claim 47.

49. An article comprising the composition of claim 47.

50. A composition made by the process comprising admixing a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy, a wax-modified polymer, wherein the wax-modified polymer comprises a wax and a polymer, wherein the wax is covalently bonded to the polymer, and zeolite, wherein the polyester has a glass transition temperature greater than −30° C.

51. A method for imparting odor-resistance to an article, comprising contacting the article with the composition of claim 50.

52. An article comprising the composition of claim 50.

53. A composition made by the process comprising admixing a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy, a wax-modified polymer, wherein the wax-modified polymer comprises a wax and a polymer, wherein the wax is covalently bonded to the polymer, and zeolite, wherein an amine compound or a hydrazine compound is not added to the mixture, wherein the amine compound has a particle diameter less than or equal to 20 µm.

54. A method for imparting odor-resistance to an article, comprising contacting the article with the composition of claim 53.

55. An article comprising the composition of claim 53.

56. A composition made by the process comprising admixing a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy, a wax-modified polymer, wherein the wax-modified polymer comprises a wax and a polymer, wherein the wax is covalently bonded to the polymer, and zeolite, wherein the zeolite comprises a mixture of $SiO_2$, $Al_2O_3$, and $Na_2O$.

57. A method for imparting odor-resistance to an article, comprising contacting the article with the composition of claim 56.

58. An article comprising the composition of claim 56.

59. A composition made by the process comprising admixing a polyester, wherein the polyester is not derived from a polyoxyalkylene glycol, and the polyester comprises an aryl group, wherein the aryl group is unsubstituted or substituted with one or more groups consisting of alkyl, alkynyl, aryl, halide, nitro, amino, ketone, aldehyde, and alkoxy; a wax-modified polymer, wherein the wax-modified polymer comprises a wax and a polymer, wherein the wax is covalently bonded to the polymer; and activated carbon, wherein the polyester has a glass transition temperature of greater than −30° C.

60. A method for imparting odor-resistance to an article, comprising contacting the article with the composition of claim 59.

61. An article comprising the composition of claim 59.

62. A composition comprising (a) a polyester, wherein the polyester consists of residues of a dicarboxylic acid and a diol, wherein the polyester is not derived from a polyoxyalkylene glycol, and when the polyester comprises an aryl group, the aryl group is unsubstituted or substituted with one or more groups consisting of alkyl, alkynyl, aryl, halide, nitro, amino, ketone, aldehyde, and alkoxy; (b) a wax-modified polymer, wherein the wax-modified polymer comprises a wax and a polymer, wherein the wax is covalently bonded to the polymer; and (c) a zeolite, wherein the polyester has a glass transition temperature greater than −30° C.

* * * * *